United States Patent
Ahmed et al.

(10) Patent No.: US 8,148,560 B2
(45) Date of Patent: Apr. 3, 2012

(54) VAGINAL TABLETS COMPRISING MISOPROSTOL AND METHODS OF MAKING AND USING THE SAME

(75) Inventors: Salah U. Ahmed, New City, NY (US); Raj R. Mahajan, Lodi, NJ (US)

(73) Assignee: Teva Women's Health, Inc., Woodcliff Lake, NJ (US)

( * ) Notice: Subject to any disclaimer, the term of this patent is extended or adjusted under 35 U.S.C. 154(b) by 1071 days.

(21) Appl. No.: 11/526,240

(22) Filed: Sep. 25, 2006

(65) Prior Publication Data

US 2007/0071814 A1 Mar. 29, 2007

Related U.S. Application Data

(60) Provisional application No. 60/719,587, filed on Sep. 23, 2005.

(51) Int. Cl.
*C07C 59/147* (2006.01)
*A61F 6/12* (2006.01)

(52) U.S. Cl. .................................. 554/119; 424/430

(58) Field of Classification Search .................. 424/430; 554/119
See application file for complete search history.

(56) References Cited

U.S. PATENT DOCUMENTS

| | | | |
|---|---|---|---|
| 4,301,146 A | 11/1981 | Sanvordeker | |
| 4,693,887 A | 9/1987 | Shah | |
| 5,015,481 A * | 5/1991 | Franz et al. | 424/494 |
| 5,017,382 A | 5/1991 | Embrey et al. | |
| 5,232,704 A | 8/1993 | Franz et al. | |
| 5,491,171 A | 2/1996 | Nishimura et al. | |
| 5,611,971 A * | 3/1997 | Maedera et al. | 264/4.1 |
| 5,877,216 A | 3/1999 | Place et al. | |
| 5,889,051 A | 3/1999 | Chen et al. | |
| 5,935,939 A * | 8/1999 | Kararli et al. | 514/54 |
| 6,046,240 A | 4/2000 | See | |
| 6,242,004 B1 | 6/2001 | Rault | |
| 6,472,434 B1 | 10/2002 | Place et al. | |
| 6,664,290 B1 * | 12/2003 | El-Rafaey | 514/530 |
| 2001/0051656 A1 | 12/2001 | Place et al. | |
| 2002/0106408 A1 | 8/2002 | Bacon et al. | |
| 2003/0050620 A1 | 3/2003 | Odidi et al. | |
| 2004/0001887 A1 | 1/2004 | Levine et al. | |

FOREIGN PATENT DOCUMENTS

| | | |
|---|---|---|
| BR | PI 0 101 039-5 A | 11/2002 |
| WO | WO 99/65496 A1 | 12/1999 |
| WO | WO 2006/099618 A1 | 9/2006 |

OTHER PUBLICATIONS

Sherman, "Pharmaceutical Tablets Comnprising an NSAID and a Prostagladin", Dec. 23, 1999, International Application Published Under the PCT, WO 99/65496. (See IDS submission).*
Toppozada et al., "Oral or Vaginal Misoprostol for Induction of Labor", Feb. 1997, International Journal of Gynecology & Obstertics, vol. 56 Iss. 2, pp. 135-139.*
Crane, J.M.G., et al., "Excessive Uterine Activity Accompanying Induced Labor," *Obstetrics and Gynecology* 97:926-931, Elsevier Science Inc. (2001).
Feitosa, F.E.L., et al., "Sublingual vs. vaginal misoprostol for induction of labor," *International Journal of Gynecology and Obstetrics* 94:91-95, Elsevier Ireland Ltd. (2006).
Meydanli, M.M., et al., "Labor induction post-term with 25 micrograms vs. 50 micrograms of intravaginal misoprostol," *International Journal of Gynecology and Obstetrics* 81:249-255, Elsevier Science Ireland Ltd. (2003).
Zieman, M., et al., "Absorption Kinetics of Misoprostol With Oral or Vaginal Administration," *Obstetrics and Gynecology* 90:88-92, Elsevier Science Inc. (1997).
International Search Report/Written Opinion for International Application No. PCT/US2006/037365, mailed on Sep. 24, 2007, European Patent Office, Netherlands.
Cytotec® misoprostol tablets label, revised Sep. 2009.

\* cited by examiner

*Primary Examiner* — Karlheinz R Skowronek
*Assistant Examiner* — Ali Soroush
(74) *Attorney, Agent, or Firm* — Panelli Haag PLLC

(57) ABSTRACT

The present invention is directed to vaginal tablets comprising misoprostol and a pharmaceutically acceptable pH insensitive, hydrophilic cellulose material, wherein the vaginal tablets do not contain a hydrophobic release controlling agent, and wherein the misoprostol and the pharmaceutically acceptable pH insensitive, hydrophilic cellulose material are in a ratio of about 1:50 to about 1:800, and wherein the vaginal tablets do not substantially change the pH of a vaginal tract.

26 Claims, 2 Drawing Sheets

VAGINAL TABLETS COMPRISING MISOPROSTOL AND METHODS OF MAKING AND USING THE SAME

Figure 1A:
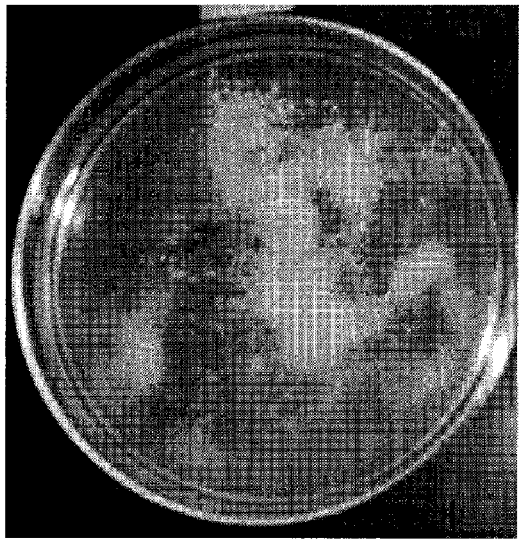

This application claims the benefit of the filing date of U.S. Appl. No. 60/719,587, filed Sep. 23, 2005, the entirety of which is fully incorporated by reference herein.

BACKGROUND OF THE INVENTION

1. Field of the Invention

The present invention is directed to vaginal tablets comprising misoprostol and a pharmaceutically acceptable pH insensitive, hydrophilic cellulose material, wherein the vaginal tablets do not contain a hydrophobic release controlling agent, and wherein the misoprostol and the pharmaceutically acceptable pH insensitive, hydrophilic cellulose material are in a ratio of about 1:50 to about 1:800, and wherein the vaginal tablets do not substantially change the pH of a vaginal tract.

2. Background Art

Pharmaceutical products have been traditionally administered via an oral, pulmonary or subcutaneous routes. However, for many pharmaceutical products, vaginal administration is a preferred route. Vaginal administration can be preferred since it allows active agents to quickly enter the bloodstream. Additionally, vaginal administration allows an active agent to avoid first pass hepatic degradation. In some instances, an active agent acts locally in the vaginal tract, and thus vaginal administration can avoid any side effects associated with systemic administration.

Misoprostol is a synthetic prostaglandin $E_1$ chemical derivative, used to prevent ulcers in people who take certain arthritis or pain medicines, including aspirin, that can cause ulcers. Misoprostol protects the stomach lining and decreases stomach acid secretion. Additionally, misoprostol has been shown to induce uterine contractions and to promote the softening of the cervix.

The common mode of adminstration of misoprostol is via oral tablets. For example, the commercial product Cytotec® (GD Searle & Co., Skokie, Ill.) is an oral tablet containing 100 µg or 200 µg of misoprostol. Misoprostol is known to degrade to a prostaglandin in the presence of water. Thus, commercial misoprostol oral tablets often contain hydrophobic excipients.

There exists a need in the art for a vaginal tablet comprising misoprostol which promotes the stability of misoprostol while still achieving the desired release rate.

BRIEF SUMMARY OF THE INVENTION

The present invention is directed to a vaginal tablet comprising misoprostol and a pharmaceutically acceptable pH insensitive, hydrophilic cellulose material, wherein the vaginal tablet does not contain a hydrophobic release controlling agent, wherein the misoprostol and the pharmaceutically acceptable pH insensitive, hydrophilic cellulose material are in a ratio of about 1:50 to about 1:800, and wherein the vaginal tablet does not substantially change the pH of a vaginal tract.

The pharmaceutically acceptable pH insensitive, hydrophilic cellulose material of the present invention can be, but is not limited to, hydroxypropyl cellulose, hydroxyethyl cellulose, hydroxypropyl methylcellulose, microcrystalline cellulose, carboxymethyl cellulose, powdered cellulose, and combinations thereof. In some embodiments, the pharmaceutically acceptable pH insensitive, cellulose material is hydroxypropyl methylcellulose.

The vaginal tablet of the present invention can further comprise a pharmaceutically acceptable hydrophilic excipient. The pharmaceutically acceptable hydrophilic excipient can be, but is not limited to, disintegrants, diluents, and combinations thereof. Disintegrants can include crospovidone, sodium starch glycolate, corn starch, and combinations thereof. In some embodiments, the disintegrant is corn starch. Diluents can include lactose, mannitol, xylitol, microcrystalline cellulose, sugar, dextrin, hydrophilic carbohydrate, and combinations thereof. In some embodiments, the diluent is lactose.

The vaginal tablet of the present invention can further comprise a pharmaceutically acceptable lubricant. Pharmaceutically acceptable lubricants can include colloidal silicon dioxide, calcium stearate, magnesium stearate, sodium stearyl fumarate, talc, stearic acid, hydrogenated vegetable oil, and combinations thereof. In some embodiments, the lubricant is magnesium stearate.

The vaginal tablet of the present invention can further comprise a coating. In some embodiments, the coating comprises hydroxypropyl methylcellulose (HPMC, methocel), hydroxymethyl cellulose, polyvinylpyrrolidone (PVP), polyethylene glycol, dextrin, maltodextrin, polyvinyl acetate- (PVA) based compounds, hydroxypropyl cellulose (HPC), cellulose acetate, cellulose phthalate, derivatives thereof, or combinations thereof. In some embodiments, the coating comprises an Opadry® coating (e.g., Colorcon Pharmaceuticals, West Point, Pa.).

In some embodiments, the vaginal tablet of claim is a controlled release tablet. In some embodiments, the misoprostol is immediately released from the controlled release tablet.

The immediate release vaginal tablet can comprise misoprostol and a pharmaceutically acceptable pH insensitive, hydrophilic cellulose material in a ratio of about 1:50 to about 1:200, in a ratio of about 1:70 to about 1:150, or in a ratio of about 1:90 to about 1:120. In some embodiments, the controlled release vaginal tablet comprises misoprostol and a pharmaceutically acceptable pH insensitive, hydrophilic cellulose material in a ratio of about 1:100.

The vaginal tablet of the present invention can be a sustained release tablet. In some embodiments, the misoprostol is continuously released from the controlled release tablet for up to 24 hours. In some embodiments, the misoprostol is continuously released from the controlled release tablet for up to 12 hours. In some embodiments, the misoprostol is continuously released from the controlled release tablet for up to 6 hours. In some embodiments, the misoprostol is continuously released from the controlled release tablet for up to 2 hours.

The sustained release vaginal tablet can comprise misoprostol and a pharmaceutically acceptable pH insensitive, hydrophilic cellulose material in a ratio of about 1:200 to about 1:800, in a ratio of about 1:300 to about 1:700, or in a ratio of about 1:400 to about 1:600. In some embodiments, the sustained release vaginal tablet can comprise misoprostol and a pharmaceutically acceptable pH insensitive, hydrophilic cellulose material in a ratio of about 1:500.

In some embodiments, the present invention is directed to a dispersible vaginal tablet comprising misoprostol and a pharmaceutically acceptable pH insensitive, hydrophilic cellulose material, wherein the vaginal tablet does not contain a hydrophobic release controlling agent, wherein the misoprostol and the pharmaceutically acceptable pH insensitive, hydrophilic cellulose material are in a ratio of about 1:50 to about 1:800, wherein the vaginal tablet does not substantially change the pH of a vaginal tract, and wherein the tablet does not flake when it comes in contact with an aqueous environment.

In some embodiments, the present invention is directed to a vaginal tablet comprising misoprostol and a pharmaceutically acceptable pH insensitive, hydrophilic cellulose material, wherein the vaginal tablet does not contain a hydrophobic release controlling agent, wherein the misoprostol and the pharmaceutically acceptable pH insensitive, hydrophilic cellulose material are in a ratio of about 1:50 to about 1:800, wherein the vaginal tablet does not substantially change the pH of a vaginal tract, and wherein the tablet adheres to an epithelial membrane.

The present invention is also directed to a method of making an immediate release vaginal tablet comprising misoprostol and a pharmaceutically acceptable pH insensitive, hydrophilic cellulose material, the method comprising: (a) dissolving misoprostol in alcohol; (b) mixing the misoprostol solution of (a) with a pharmaceutically acceptable pH insensitive, hydrophilic cellulose material to form a misoprostol/cellulose mixture, wherein the ratio of misoprostol to pharmaceutically acceptable pH insensitive, hydrophilic cellulose material is about 1:50 to about 1:200; (c) mixing the misoprostol/cellulose mixture of (b) with a pharmaceutically acceptable excipient to form a misoprostol/cellulose/excipient mixture; and (d) compressing the misoprostol/cellulose/excipient mixture of (c) into a vaginal tablet, wherein the vaginal tablet does not contain a hydrophobic release controlling agent. In some embodiments, the method further comprises (e) coating the vaginal tablet of (d) with a coating. The coating of (e) can comprise hydroxypropyl methylcellulose, polyethylene glycol, dextrin, maltodextrin, or combinations thereof.

The present invention is also directed to a method of making a sustained release vaginal tablet comprising misoprostol and a pharmaceutically acceptable pH insensitive, hydrophilic cellulose material, the method comprising: (a) dissolving misoprostol in alcohol; (b) mixing the misoprostol solution of (a) with a pharmaceutically acceptable pH insensitive, hydrophilic cellulose material to form a misoprostol/cellulose mixture, wherein the ratio of misoprostol to pharmaceutically acceptable pH insensitive, hydrophilic cellulose material is about 1:200 to about 1:800; (c) mixing the misoprostol/cellulose mixture of (b) with a pharmaceutically acceptable excipient to form a misoprostol/cellulose/excipient mixture; and (d) compressing the misoprostol/cellulose/excipient mixture of (c) into a vaginal tablet, wherein the vaginal tablet does not contain a hydrophobic release controlling agent. In some embodiments, the method further comprises (e) coating the vaginal tablet of (d) with a coating. The coating of (e) can comprise hydroxypropyl methylcellulose, polyethylene glycol, dextrin, maltodextrin, or combinations thereof.

The present invention is also directed to a method of inducing cervical ripening in a female in need thereof, the method comprising vaginally administering to the female the vaginal tablet of the present invention. The present invention is also directed to a method of inducing uterine contractions in a female in need thereof, the method comprising vaginally administering to the female the vaginal tablet of the present invention.

BRIEF DESCRIPTION OF THE DRAWINGS/FIGURES

Figure 1B:
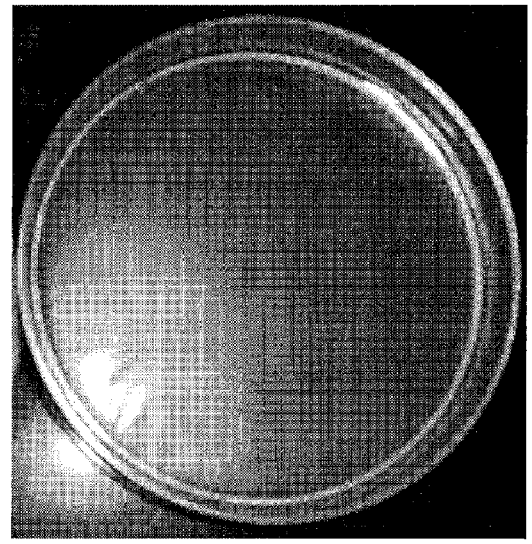

FIG. 1 demonstrates the difference in clarity between (A) a Cytotec® oral tablet, and (B) a vaginal tablet of the present invention as described in Example 1 (but without misoprostol). The picture under (A) shows a cloudy aqueous composition containing flakes from the Cytotec® oral tablet, wherein the oral tablet has not completely dispersed. The picture under (B) shows a clear aqueous composition, wherein the vaginal tablet has dispersed almost to completion.

Figure 2A:
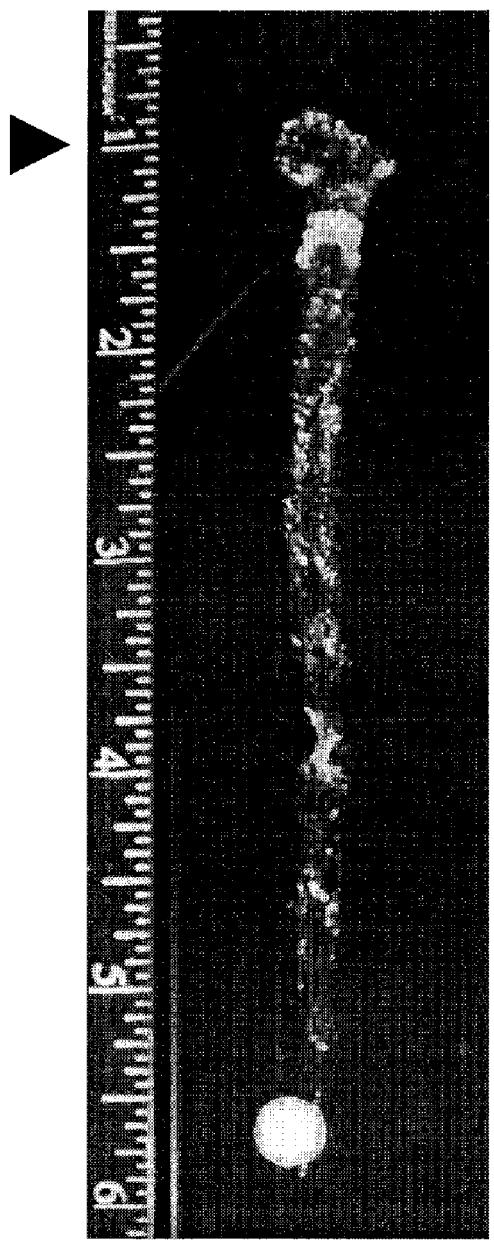
Figure 2B:
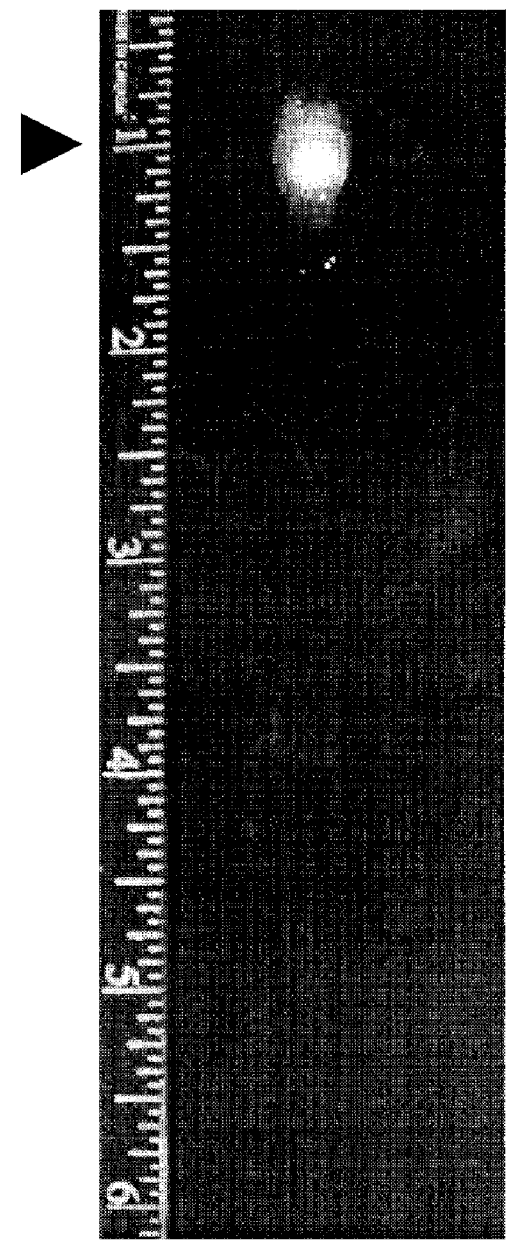

FIG. 2 demonstrates the adhesive properties of (A) a Cytotec® oral tablet, and (B) a vaginal tablet of the present invention as described in Example 1 (but without misoprostol). The arrow indicates the original position of the tablets. As is demonstrated on the picture, the Cytotec® oral tablet slides when the plate is tilted, whereas the vaginal tablet adheres to the plate and does not slide.

DETAILED DESCRIPTION OF THE INVENTION

The present invention is directed to a vaginal tablet comprising misoprostol and a pharmaceutically acceptable pH insensitive, hydrophilic cellulose material, wherein the vaginal tablet does not contain a hydrophobic release controlling agent, wherein the misoprostol and the pharmaceutically acceptable pH insensitive, hydrophilic cellulose material are in a ratio of about 1:50 to about 1:800, and wherein the vaginal tablet does not substantially change the pH of a vaginal tract.

Misoprostol is a synthetic analogue of a naturally occurring prostaglandin $E_1$. Misoprostol is chemically described as (±)methyl 11α, 16-dihydroxy-16-methyl-9-oxoprost-13E-en-1-oate and has the generic chemical structure:

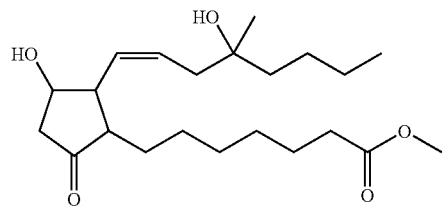

Misoprostol contains approximately equal amounts of two diastereomers, each being a racemic mixture of two optical isomers. The four isomers are SC-30422, SC-30423, SC-30248 and SC-30249, with isomer SC-30429 being the primary active form. Misoprostol is water soluble and water labile.

In the present invention, misoprostol is provided in a vaginal tablet. "Vaginal tablet" refers to a dosage tablet having a size and shape convenient for placement in the vaginal tract. The term "tablet" refers to a compressed or molded block of a solid material. The term "vaginal" refers to the intended location of administration, which includes the entire vaginal tract, including the cervix of a female.

A vaginal tract presents different properties than the environment of a tablet taken orally, i.e., the mouth and/or the gastrointestinal tract. For example, the environment of the vaginal tract has less fluid than the environment of mouth or stomach. Thus, in some embodiments it is important that the vaginal tablet be capable of dissolving in a reduced amount of water. Additionally, in some embodiments, it is desired that the vaginal tablet of the present invention adhere to the vaginal tract whereas in some embodiments if may not be desirable that an oral tablet adhere to the mouth and/or gastrointestinal tract.

In some embodiments, more complete dispersion of the tablet in the vaginal tract can provide better delivery of the misoprostol to the subject. In some embodiments, more complete dispersion can provide a more consistent release profile of the misoprostol. In some embodiments, more complete dispersion can provide a reduced amount of tablet residue. In some instances, any tablet residue can cause a "gritty" sensation, or provide irritation to the vaginal lining. Thus, in some embodiments, the tablet of the present invention provides for administration of misoprostol to a vaginal tract with reduced gritty residue and/or reduced irritation relative to administration of an oral tablet, e.g., Cytotec®.

The term "pharmaceutically acceptable" refers to compounds or compositions which are, within the scope of sound medical judgment, suitable for contact with the tissues of human beings and animals without excessive toxicity, irritation, allergic response, or other problem complications commensurate with a reasonable benefit/risk ratio.

The term "pH insensitive" refers to compounds which neither easily provide, nor easily accept hydronium ions. The term "pH insensitive" also refers to compounds that are not ionizable. For example, a pH insensitive cellulose material would not substantially change the pH of an unbuffered solution when placed in an unbuffered solution.

The term "hydrophilic" refers to a property of a compound, wherein the compound has a strong affinity for water or other polar solvents.

The term "cellulose material" of the present invention refers to polymers of cellulose, and derivatives thereof, of the general formula:

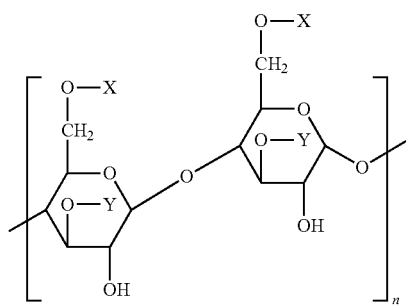

wherein n is the degree of polymerization, X is hydrogen or $C_1$-$C_{12}$ alkyl, and Y is hydrogen or $C_1$-$C_{12}$ alkyl, wherein alkyl can be optionally substituted with one or more hydroxy. In some embodiments, X is hydrogen, methyl, ethyl, propyl, or butyl, optionally substituted with one to three hydroxy. In some embodiments, Y is hydrogen, methyl, ethyl, propyl, or butyl, optionally substituted with one to three hydroxy. Additionally, the degree of polymerization n can vary. For example, in some embodiments, n is from 10 to 1000, or from 20 to 400. In some embodiments, the cellulose material includes one or more types of cellulose chains, wherein the cellulose chains can have different values of n. In some embodiments, the cellulose material can take a defined three-dimensional shape that provides desirable physical characteristics, e.g., in the case of microcrystalline cellulose, the cellulose material forms a crystal lattice.

Various hydrophilic cellulose materials can be used. For example, pharmaceutically acceptable pH insensitive, hydrophilic cellulose materials can be, but are not limited to, cellulose (e.g., microcrystalline cellulose and powdered cellulose), methyl cellulose, hydroxyethylcellulose, hydroxypropyl cellulose, hydroxyethyl cellulose, hydroxypropyl methylcellulose, carboxymethyl cellulose, and combinations thereof. In some embodiments, the pharmaceutically acceptable pH insensitive, cellulose material is hydroxypropyl methylcellulose. The cellulose materials of the present invention can vary in molecular weight. In some embodiments, the cellulose material can be a molecular weight grade of about 90,000 molecular weight (MW) to about 1,500,000 MW. In some embodiments, the cellulose material can be a molecular weight of about 100,000 MW to about 1,000,000 MW. In some embodiments, the cellulose material can be about 150,000 MW to about 750,000 MW.

The vaginal tablet of the present invention can further comprise a pharmaceutically acceptable hydrophilic excipient. The term "excipient" refers to a substance that is used in the formulation of pharmaceutical compositions, and, by itself, generally has little or no therapeutic value.

Acceptable pharmaceutically acceptable hydrophilic excipients include, but are not limited to disintegrants, diluents, and combinations thereof. In some embodiments, the hydrophilic excipients are water dispersible or water soluble. Disintegrants can include crospovidone, sodium starch glycolate, corn starch, and combinations thereof. In some embodiments, the disintegrant is corn starch. Diluents can include lactose, mannitol, xylitol, microcrystalline cellulose, sugar, dextrin, hydrophilic carbohydrate, and combinations thereof. In some embodiments, the diluent is lactose.

In some embodiments, the hydrophilic cellulose material, hydrophilic excipients, and/or lubricants are water dispersible. The amount of water dispersible components in the vaginal tablet of the present invention can vary. In some embodiments, the vaginal tablet can comprise greater than about 50%, greater than about 60%, greater than about 70%, greater than about 80%, or greater than about 90% (w/w) water dispersible components.

The vaginal tablet of the present invention can further comprise a pharmaceutically acceptable lubricant. Pharmaceutically acceptable lubricants can include, but are not limited to, colloidal silicon dioxide, calcium stearate, magnesium stearate, sodium stearyl fumarate, talc, stearic acid, hydrogenated vegetable oil, and combinations thereof. In some embodiments, the lubricant is magnesium stearate.

The vaginal tablet can further comprise a coating. In some embodiments, the coating comprises hydroxypropyl methylcellulose (HPMC, methocel), hydroxymethyl cellulose, polyvinylpyrrolidone (PVP), polyethylene glycol, dextrin, maltodextrin, polyvinyl acetate- (PVA) based compounds, hydroxypropyl cellulose (HPC), cellulose acetate, cellulose phthalate, derivatives thereof, or combinations thereof. For example, in some embodiments, an Opadry® coating (Colorcon Pharmaceuticals) can be used.

The vaginal tablet of the present invention does not contain a hydrophobic release controlling agent. The term "hydrophobic release controlling agent" refers to any compound that is substantially insoluble in water whose presence in a formulation alters the release rate of the active agent from the formulation. Examples of hydrophobic release controlling agents include, but are not limited to, oils, e.g., hydrogenated vegetable oil, castor oil, etc., carbomers, carbowax, and combinations thereof. Since the vaginal tract is an aqueous environment, the absence of a hydrophobic release controlling agent can result in reduced residual material in the vaginal tract after the vaginal tablet has been administered. The presence of a hydrophobic release controlling agent can result in a gritty residue. Thus, in some embodiments, vaginal tablets that do not contain hydrophobic release controlling agents have reduced amounts of gritty residue. Additionally, hydrophobic release controlling agents can reduce the release rate of the active agent from the vaginal tablet in the vaginal tract.

Reduced release rates from a vaginal tablet can be undesirable for immediate release vaginal tablet formulations.

The vaginal tablet of the present invention can have various release profiles. For example, the release profile of the tablet can be controlled release, i.e., the misoprostol is released at a specific release rate for a specific amount of time, or sustained release, i.e., the misoprostol is continually released over an extended period of time. In some embodiments, the vaginal tablet of claim is a sustained release tablet. In some embodiments, the misoprostol is immediately released from the controlled release tablet.

The immediate controlled release vaginal tablet can comprise misoprostol and a pharmaceutically acceptable pH insensitive, hydrophilic cellulose material in a ratio of about 1:50 to about 1:200, in a ratio of about 1:70 to about 1:150, or in a ratio of about 1:90 to about 1:120. In some embodiments, the controlled release vaginal tablet comprises misoprostol and a pharmaceutically acceptable pH insensitive, hydrophilic cellulose material in a ratio of about 1:100.

In some embodiments of the present invention, the immediate release vaginal tablets of the present invention as described herein dissolve quicker and more completely in the vaginal tract than tablets formulated for oral delivery. In some embodiments, greater than 90%, greater than 92%, greater than 95%, greater than 96%, greater than 97%, greater than 98%, or greater than 99% of the tablet disintegrates in the vaginal tract within 30 minutes. In some embodiments, greater than 90%, greater than 92%, greater than 95%, greater than 96%, greater than 97%, greater than 98%, or greater than 99% of the tablet disintegrates in the vaginal tract within 20 minutes. In some embodiments, greater than 90%, greater than 92%, greater than 95%, greater than 96%, greater than 97%, greater than 98%, or greater than 99% of the tablet disintegrates in the vaginal tract within 10 minutes.

The vaginal tablet of the present invention can be a sustained release tablet. In some embodiments, the misoprostol is continuously released from the sustained release tablet for up to 24 hours. In some embodiments, the misoprostol is continuously released from the sustained release tablet for up to 12 hours. In some embodiments, the misoprostol is continuously released from the sustained release tablet for up to 6 hours. In some embodiments, the misoprostol is continuously released from the sustained release tablet for up to 2 hours.

The sustained release vaginal tablet can comprise misoprostol and a pharmaceutically acceptable pH insensitive, hydrophilic cellulose material in a ratio of about 1:200 to about 1:800, in a ratio of about 1:300 to about 1:700, or in a ratio of about 1:400 to about 1:600. In some embodiments, the sustained release vaginal tablet can comprise misoprostol and a pharmaceutically acceptable pH insensitive, hydrophilic cellulose material in a ratio of about 1:500.

The vaginal tablet of the present invention can comprise various amounts of misoprostol. In some embodiments, the vaginal tablet can comprise about 10 μg to about 100 μg, about 10 μg to about 90 μg, about 20 μg to about 80 μg, about 30 μg to about 70 μg, or about 40 μg to about 60 μg of misoprostol.

In some embodiments, the vaginal tablet of the present invention does not flake when placed in an aqueous environment. The term "flake" refers to the formation of particles when the tablet is dispersed. In some embodiments, these flakes can be, but are not limited to, particles planar in shape. These flakes can alter the dissolution profile of the misoprostol, increase discomfort to the subject being treated, and cause a gritty residue to form in the vaginal tract.

In some embodiments, the vaginal tablet of the present invention adheres to the vaginal tract of the subject being treated. In some embodiments, the adherence is to the vaginal epithelial membrane. In some embodiments, the adherence remains until the tablet is dispersed.

The present invention is also directed to a method of making an immediate release vaginal tablet comprising misoprostol and a pharmaceutically acceptable pH insensitive, hydrophilic cellulose material, the method comprising: (a) dissolving misoprostol in alcohol; (b) mixing the misoprostol solution of (a) with a pharmaceutically acceptable pH insensitive, hydrophilic cellulose material to form a misoprostol/cellulose mixture, wherein the ratio of misoprostol to pharmaceutically acceptable pH insensitive, hydrophilic cellulose material is about 1:50 to about 1:200; (c) further mixing the misoprostol/cellulose mixture of (b) with a pharmaceutically acceptable excipient to form a misoprostol/cellulose/excipient mixture; and (d) compressing the misoprostol/cellulose/excipient mixture of (c) into a vaginal tablet, wherein the vaginal tablet does not contain a hydrophobic release controlling agent. In some embodiments, the method further comprises (e) coating the vaginal tablet of (d) with a coating. The coating of (e) can comprise hydroxypropyl methylcellulose, polyethylene glycol, dextrin, maltodextrin, and combinations thereof.

The present invention is also directed to a method of making a sustained release vaginal tablet comprising misoprostol and a pharmaceutically acceptable pH insensitive, hydrophilic cellulose material, the method comprising: (a) dissolving misoprostol in alcohol; (b) mixing the misoprostol solution of (a) with a pharmaceutically acceptable pH insensitive, hydrophilic cellulose material to form a misoprostol/cellulose mixture, wherein the ratio of misoprostol to pharmaceutically acceptable pH insensitive, hydrophilic cellulose material is about 1:200 to about 1:800; (c) further mixing the misoprostol/cellulose mixture of (b) with a pharmaceutically acceptable excipient to form a misoprostol/cellulose/excipient mixture; and (d) compressing the misoprostol/cellulose/excipient mixture of (c) into a vaginal tablet, wherein the vaginal tablet does not contain a hydrophobic release controlling agent. In some embodiments, the method further comprises (e) coating the vaginal tablet of (d) with a coating. The coating of (e) can comprise hydroxypropyl methylcellulose, polyethylene glycol, dextrin, maltodextrin, and combinations thereof.

The present invention is also directed to a method of inducing cervical ripening in a female in need thereof, the method comprising vaginally administering to the female the vaginal tablet of the present invention. This method is intended to encompass situations wherein the female is in medical need of cervical ripening or wherein the female voluntarily chooses to induce cervical ripening without the presence of medical necessity. The present invention is also directed to a method of inducing uterine contractions in a female in need thereof, the method comprising vaginally administering to the female the vaginal tablet of the present invention. This method is intended to encompass situations wherein the female is in medical need of the inducement of uterine contractions or wherein the female voluntarily chooses to induce uterine contractions without the presence of medical necessity.

All of the various embodiments or options described herein can be combined in any and all variations.

The following examples serve only to illustrate the invention, and is not to be construed in any way to limit the invention.

EXAMPLE 1

An immediate release vaginal tablet was prepared using the ingredients and amounts described in Table 1.

TABLE 1

| Ingredients | mg/tablet |
|---|---|
| GRANULATION | |
| Misoprostol | 0.1 |
| Lactose Monohydrate, NF (Fast Flo) | 18 |
| Hydroxypropyl Methylcellulose 1910, USC (Methocel ® E15-LV Premium) | 10 |
| Alcohol, USP | * |
| POST GRANULATION | |
| Corn Starch, NF | 15 |
| Anhydrous Lactose, NF (DT Grade) | 36.7 |
| FINAL MIXING | |
| Magnesium Stearate, NF | 0.2 |
| CORE TABLET WEIGHT | 80 |

*Alcohol is not present in the final formulation.

Hydroxypropyl methylcellulose (HPMC) and lactose monohydrate were mixed together, passed through a Russell Finex Compact Sieve (#30 screen), then placed in a Collette Gral 300 Liter high shear mixer and mixed. Then misoprostol, which had previously been dissolved in ethyl alcohol, was sprayed onto the HPMC/Lactose monohydrate mixture, while the mixture was still being mixed to form a wet granulate. Once the misoprostol solution had been applied, an ethanol rinse solution was sprayed into the mixer to form a rinsed wet granulate. The rinsed wet granulate was then placed in a fluid bed dryer and air purged for 30 minutes at 30° C., followed by drying at 55° C. until the moisture content of the mixture was about 0.8%. The dried granulate was then passed through a Fitzmill Model D equipped with a 1536-0080 screen at high speed and hammers forward, then placed in a Collette Gral 300 Liter High Shear Mixer. The milled, dried granulate was then mixed for 1 minute with corn starch that had previously passed through a #30 mesh screen. Following addition of the corn starch, anhydrous lactose that had previously passed through a #30 mesh screen was added to the mixture, followed by addition of magnesium stearate and a final one minute mixing. The final composition was then compressed in a Kikusui tabletting press to create a vaginal tablet.

EXAMPLE 2

A sustained release vaginal tablet was prepared using the ingredients and amount described in Table 2.

TABLE 2

| Ingredients | Mg/tablet |
|---|---|
| GRANULATION | |
| Misoprostol | 0.1 |
| Lactose Monohydrate, NF (Fast Flo) | 18 |
| Hydroxypropyl Methylcellulose 1910, USC (Methocel ® E15-LV Premium) | 7 |
| Alcohol, USP | * |
| POST GRANULATION | |
| Hydroxypropyl Methylcellulose 1910, USC (Methocel ® E15-LV Premium) | 44.7 |
| Corn Starch, NF | 10 |
| FINAL MIXING | |
| Magnesium Stearate, NF | 0.2 |
| CORE TABLET WEIGHT | 80 |

*Alcohol is not present in the final formulation.

Hydroxypropyl methylcellulose (HPMC) and lactose monohydrate were mixed together, passed through a Russell Finex Compact Sieve (#30 screen), then placed in a Collette Gral 300 Liter high shear mixer and mixed. Then misoprostol, which had previously been dissolved in ethyl alcohol, was sprayed onto the HPMC/Lactose monohydrate mixture, while the mixture was still being mixed, to form a wet granulate. Once the misoprostol solution had been applied, an ethanol rinse solution was sprayed into the mixer to form a rinsed wet granulate. The rinsed wet granulate was then placed in a fluid bed dryer and air purged for 30 minutes at 30° C., followed by drying at 55° C. until the moisture content of the mixture was about 0.8%. The dried granulate was then passed through a Fitzmill Model D equipped with a 1536-0080 screen at high speed and hammers forward, then placed in a Collette Gral 300 Liter High Shear Mixer. The milled, dried granulate was then mixed for 1 minute with hydroxypropyl methylcellulose and corn starch that had previously passed through a #30 mesh screen. Following addition of the corn starch, anhydrous lactose that had previously passed through a #30 mesh screen was added to the mixture, followed by addition of magnesium stearate and a final one minute mixing. The final composition was then compressed in a Kikusui tabletting press to create a vaginal tablet.

EXAMPLE 3

The dispersion profile of the immediate release vaginal tablet as described in Example 1 (but without the addition of misoprotol) was compared to the dispersion profile of the Cytotec® misoprostol oral tablet. One vaginal tablet as described in Example 1 was placed in a beaker containing 10 mL of water. For comparison purposes, one Cytotec® misoprostol oral tablet was also placed in a beaker containing 10 mL of water. The beakers were shaken for three minutes. At the end of three minutes, it was observed that the vaginal tablet as described in Example 1 dispersed more completely and the solution was more clear (less cloudy) with fewer flakes relative to the Cytotec® misoprostol oral tablet. See FIG. 1.

EXAMPLE 4

The adhesive properties of the immediate release vaginal tablet as described in Example 1 (but without the addition of misoprostol) was compared to the adhesive properties of the Cytotec® misoprostol oral tablet. Three drops of water were placed on a glass plate. Then a vaginal tablet as described in Example 1 was placed on the drops of water. The plate was then tilted at a 90 degree angle. It was observed that the vaginal tablet adhered to the glass plate and did not slide significantly on the plate. The experiment was repeated with the Cytotec® misoprostol oral tablet. However, in this case, it was observed that when the glass plate was tilted, the oral tablet slid on the glass plate. This example indicates that the adhesive property of the vaginal tablet was greater than the adhesive property of the oral tablet. See FIG. 2.

These examples illustrate possible formulations of the present invention. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A vaginal tablet comprising misoprostol and a pharmaceutically acceptable pH insensitive, hydrophilic cellulose material, wherein the vaginal tablet does not contain a hydrophobic release controlling agent, wherein the misoprostol and the pharmaceutically acceptable pH insensitive, hydrophilic cellulose material are in a ratio of about 1:50 to about 1:800, wherein the vaginal tablet does not substantially change the pH of a vaginal tract, and wherein the tablet adheres to the vaginal tract of a subject.

2. The vaginal tablet of claim 1, wherein the pharmaceutically acceptable pH insensitive, hydrophilic cellulose material is selected from the group consisting of hydroxypropyl cellulose, hydroxyethylcellulose, hydroxypropyl methylcellulose, microcrystalline cellulose, carboxymethyl cellulose, powdered cellulose, and combinations thereof.

3. The vaginal tablet of claim 2, wherein the pharmaceutically acceptable pH insensitive, cellulose material is hydroxypropyl methylcellulose.

4. The vaginal tablet of claim 1, further comprising a pharmaceutically acceptable hydrophilic excipient.

5. The vaginal tablet of claim 4, wherein the pharmaceutically acceptable hydrophilic excipient is selected from the group consisting of a disintegrant, a diluent, and combinations thereof.

6. The vaginal tablet of claim 5, wherein the pharmaceutically acceptable hydrophilic excipient is a disintegrant selected from the group consisting of a crospovidone, a sodium starch glycolate, a corn starch, and combinations thereof.

7. The vaginal tablet of claim 6, wherein the disintegrant is corn starch.

8. The vaginal tablet of claim 5, wherein the pharmaceutically acceptable hydrophilic excipient is a diluent is selected from the group consisting of lactose, mannitol, xylitol, microcrystalline cellulose, sugar, dextrin, hydrophilic carbohydrate, and combinations thereof.

9. The vaginal tablet of claim 8, wherein the diluent is lactose.

10. The vaginal tablet of claim 1, further comprising a pharmaceutically acceptable lubricant.

11. The vaginal tablet of claim 10, wherein the pharmaceutically acceptable lubricant is selected from the group consisting of colloidal silicon dioxide, calcium stearate, magnesium stearate, sodium stearyl fumarate, talc, stearic acid, and combinations thereof.

12. The vaginal tablet of claim 11, wherein the lubricant is magnesium stearate.

13. The vaginal tablet of claim 1, further comprising a coating.

14. The vaginal tablet of claim 13, wherein the coating comprises hydroxypropyl methylcellulose, hydroxymethyl cellulose, polyvinylpyrrolidone, polyethylene glycol, dextrin, maltodextrin, polyvinyl acetate-based compounds, hydroxypropyl cellulose, cellulose acetate, cellulose phthalate, derivatives thereof, or combinations thereof.

15. The vaginal tablet of claim 1, wherein the tablet is a controlled release tablet.

16. The vaginal tablet of claim 15, wherein the misoprostol is immediately released from the controlled release tablet.

17. The vaginal tablet of claim 16, wherein the misoprostol and the pharmaceutically acceptable pH insensitive, hydrophilic cellulose material are in a ratio of about 1:50 to about 1:200.

18. The vaginal tablet of claim 15, wherein the controlled release tablet is a sustained release tablet.

19. The vaginal tablet of claim 18, wherein misoprostol is continuously released from the controlled release tablet for up to 24 hours.

20. The vaginal tablet of claim 18, wherein the misoprostol and the pharmaceutically acceptable pH insensitive, hydrophilic cellulose material are in a ratio of about 1:200 to about 1:800.

21. A vaginal tablet comprising misoprostol and a pharmaceutically acceptable pH insensitive, hydrophilic cellulose material, wherein the vaginal tablet does not contain a hydrophobic release controlling agent, wherein the misoprostol and the pharmaceutically acceptable pH insensitive, hydrophilic cellulose material are in a ratio of about 1:50 to about 1:800, wherein the vaginal tablet does not substantially change the pH of a vaginal tract, and wherein the tablet adheres to an epithelial membrane.

22. A method of making a sustained release vaginal tablet comprising misoprostol and a pharmaceutically acceptable pH insensitive, hydrophilic cellulose material, the method comprising:
(a) dissolving misoprostol in alcohol;
(b) mixing the misoprostol solution of (a) with a pharmaceutically acceptable pH insensitive, hydrophilic cellulose material to form a misoprostol/cellulose mixture, wherein the ratio of misoprostol to pharmaceutically acceptable pH insensitive, hydrophilic cellulose material is about 1:200 to about 1:800;
(c) mixing the misoprostol/cellulose mixture of (b) with a pharmaceutically acceptable excipient to form a misoprostol/cellulose/excipient mixture; and
(d) compressing the misoprostol/cellulose/excipient mixture of (c) into a vaginal tablet,
wherein the vaginal tablet does not contain a hydrophobic release controlling agent; and
wherein the vaginal tablet adheres to the vaginal tract of a subject.

23. The method of claim 22, further comprising:
(e) coating the vaginal tablet of (d) with a coating.

24. The method of claim 23, wherein the coating comprises hydroxypropyl methylcellulose, polyethylene glycol, dextrin, maltodextrin, and combinations thereof.

25. A method of inducing cervical ripening in a female in need thereof, the method comprising vaginally administering to the female the vaginal tablet of claim 1.

26. A method of inducing uterine contractions in a female in need thereof, the method comprising vaginally administering to the female the vaginal tablet of claim 1.

* * * * *